United States Patent [19]
Uchida et al.

[11] Patent Number: 4,630,612
[45] Date of Patent: Dec. 23, 1986

[54] ULTRASONIC DIAGNOSTIC APPARATUS

[75] Inventors: Rokuroh Uchida; Katsuhiko Nagasaki; Yasunori Miyake, all of Tokyo; Michio Ohno, Kawasaki; Hitoshi Takeichi, Kawasaki; Hiroji Matsumoto, Kawasaki, all of Japan

[73] Assignees: Aloka Co., Ltd., Tokyo; Hayashi Electric Co., Ltd., Kanagawa, both of Japan

[21] Appl. No.: 614,432

[22] Filed: May 25, 1984

[30] Foreign Application Priority Data

May 25, 1983 [JP] Japan ................... 58-90765
May 25, 1983 [JP] Japan ................... 58-90766
May 25, 1983 [JP] Japan ................... 58-77587[U]

[51] Int. Cl.⁴ ............................... A61B 10/00
[52] U.S. Cl. ................... 128/660; 128/663
[58] Field of Search ............... 128/660-663; 73/821.25, 625-626

[56] References Cited

U.S. PATENT DOCUMENTS 4,370,985  2/1983  Takeichi et al. ............ 128/663
4,373,533  2/1983  Iinuma ........................ 128/663
4,416,286 11/1983  Iinuma et al. ............... 128/663
4,476,874 10/1984  Taenzer et al. ............. 128/663

Primary Examiner—Kyle L. Howell
Assistant Examiner—Francis J. Jaworski
Attorney, Agent, or Firm—Koda and Androlia

[57] ABSTRACT

An ultrasonic diagnostic apparatus capable of providing a B-mode tomographic image of and Doppler information on a moving member in a living subject. The apparatus comprises a cursor setting device which supplies a signal for displaying a cursor at a prescribed position on a B-mode display, echo tracking circuits which cause markers to track the image signals of a prescribed moving member at optionally selected positions on the cursor, marker setting devices for setting the initial positions of the markers, a synthesizer for synthesizing and sending to the B-mode display a B-mode image signal and marker image signals from the echo tracking circuits, and a position measuring circuit for measuring the position of the prescribed moving member on the cursor on the basis of the marker image signals from the echo tracking circuits. The apparatus can display a moving member, for example a blood vessel, within the subject as a B-mode picture which tracks the position of the moving member as it moves and can further electrically output the position of the moving member. As a result, it is possible to electrically store or process the position of the blood vessel. In particular, the apparatus makes it possible to easily and accurately measure blood vessels in the circulatory system, the amount of blood flowing through such vessels, and the volume of internal organs.

11 Claims, 12 Drawing Figures

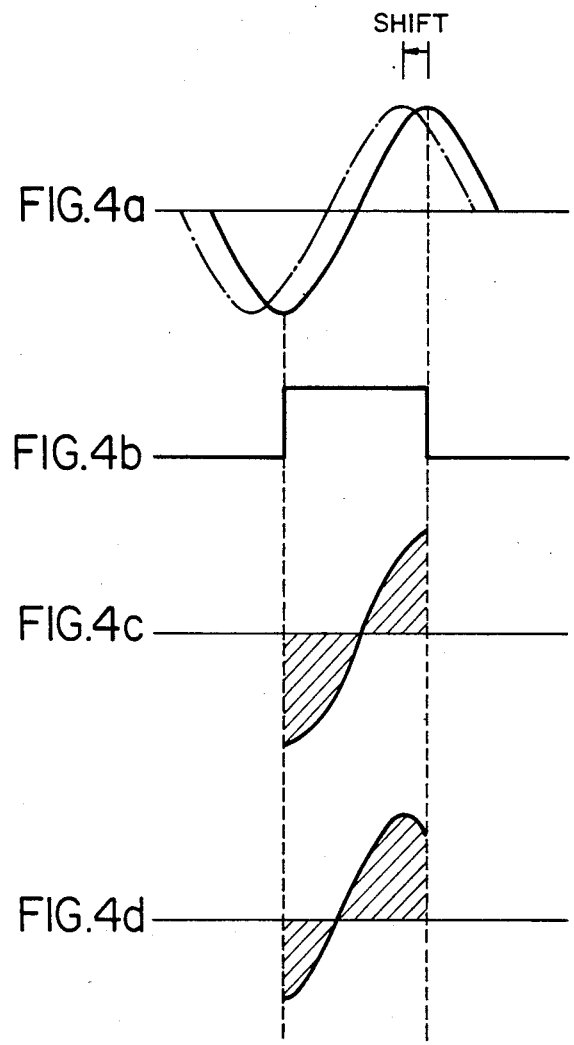

4,630,612

ULTRASONIC DIAGNOSTIC APPARATUS

BACKGROUND OF THE INVENTION

1. Field of the Invention

This invention relates to an ultrasonic diagnostic apparatus, more particularly to an improved ultrasonic diagnostic apparatus which enables noninvasive observation and examination of an afflicted portion of the circulatory system or of other tissue within the body.

2. Description of the Prior Art

The art of using ultrasonic waves in the diagnosis of diseases of the circulatory system has been practically applied in a wide range of fields. Ordinarily, ultrasonic examination of the circulatory system has fallen into two main categories: the method involving the imaging of various organs and the method involving the measurement of the flow velocity of blood and other body fluids. The former of these methods has been widely used to produce tomographic images of the heart, arteries and veins using A-mode imaging, B-mode imaging or a modification of one of these modes. In the latter method, ultrasonic waves are directed into the blood flow and the blood flow velocity is determined using the Doppler effect. This method is highly effective as a non-invasive means for early discovery of diseases of the circulatory system of the brain, for treatment of such diseases and for evaluation etc. of the effect of medicines on the circulatory system of the brain.

In the former method, however, there have been disadvantages in that the conventionally employed image display device permits observation of only the tomographic image, making it necessary to derive numerical values by measuring the displayed image and complicating the diagnostic procedure, and in that it has been difficult to electrically store the data derived by such measurement together with the image. As a result, this method has had little practicability in actual diagnostic situations.

In particular, it has been extremely difficult to make accurate measurement in cases where the object under observation includes a moving member. Such a case arises, for example, in the examination of the heart and other organs of the circulatory system where the organ or the blood flowing through it are kept in constant motion by the pulsation of the heart.

Moreover, although the conventional methods mentioned above wherein an image is displayed through the use of an ultrasonic pulse beam or the blood flow velocity etc. are measured using the Doppler effect have been put to practical application in the examination of the circulatory system, these two methods have been employed independently of one another so that it has been impossible to carry out realtime observation of the relationship between the state of motion and the blood flow velocity in the actual portion of the organ where motion occurs. As a consequence, it has not always been possible to carry out an adeuate examination.

Another problem of the conventional methods concerns the importance of knowing the amount of arterial blood flow, particularly that in the brain circulatory system, in carrying out a proper diagnosis of diseases of the brain circulatory system. For obtaining the amount of blood flow with the conventional apparatuses, it has been necessary to separately obtain the blood vessel diameter from an A-mode image and the blood flow velocity by the Doppler effect and then to carry out a separate calculation by, for example, a computer. Te procedure is thus very complicated and is totally incapable of providing appropriate real-time diagnostic information. What is more, even the measurement of the diameter of the blood vessel cannot be carried out with precision.

In this connection it is known that when the flow velocity of blood etc. is to be measured using the Doppler effect of ultrasonic waves, it is important to properly select the angle of ultrasonic wave transmission and reception with respect to the direction of blood flow, and that optimum results are obtained when, as shown in FIG. 5, this angle is set at 60°.

In fact, however, it is generally impossible to determine the direction in which a blood vessel runs within a living body so that with the conventional apparatus the method used has been to attach a Doppler probe to the surface of the body so as to form an angle of approximately 60° with respect to the presumed direction of the blood vessel being subjected to measurement. As a result, the conventional method of measuring blood flow velocity by the Doppler effect has had the shortcoming of including a large error factor.

SUMMARY OF THE INVENTION

In view of the comments and observations made in the foregoing, the first object of the present invention is to provide an ultrasonic diagnostic apparatus which is able to track the movement of a moving member of the object under examination and display the position thereof as a B-mode image and which is capable of outputting said position as an electrical signal.

A second object of the invention is to provide an ultrasonic diagnostic apparatus which is able to provide a real-time display of the amount of blood flow in the circulatory system of the brain at the same time as providing a tomographic image of the corresponding blood vessel, for example, a carotid artery.

The third object of the invention is to provide an ultrasonic diagnostic apparatus wherein the direction of transmission and reception of a Doppler beam can be very easily set at any desired angle with respect to the direction of flow in the region to be examined.

These objects are obtained by providing an ultrasonic diagnostic apparatus comprising an ultrasonic pulse probe which transmits and receives an ultrasonic wave signal to and from a portion under examination including a moving member, a transmission/reception circuit for controlling the pulse transmission and reception operation of the ultrasonic pulse probe, a B-mode display for displaying a B-mode tomographic image on the basis of an ultrasonic B-mode image signal obtained from the transmission/reception control circuit, a cursor setting device for supplying to the transmission/reception control circuit a cursor position signal in order to display a cursor at a predetermined scan position of the B-mode display, at least one echo tracking circuit for causing at least one marker to track the video signal of the moving member at a desired position on the cursor, at least one marker setting device for supplying to the echo tracking device an initial marker signal for setting the initial position of the marker on the cursor, a synthesizer for synthesizing and sending to the B-mode display the B-mode image signal from the transmission/reception control circuit and the marker image signal from the echo tracking circuit, and a position measuring circuit for measuring the position of the moving member on the cursor on the basis of the marker image signal from the echo tracking circuit.

Moreover to achieve the second object of this invention, there is provided an ultrasonic diagnostic apparatus which, in order to enable it to provide a real-time display of the flow velocity and flow volume of a fluid in the moving member while at the same time displaying a B-mode image of the portion under examination including the moving member, comprises an ultrasonic pulse probe which transmits and receives an ultrasonic wave signal to and from a portion under examination including a moving member, a transmission/reception circuit for controlling the pulse transmission and reception operation of the ultrasonic pulse probe, a B-mode display for displaying a B-mode tomographic image on the basis of an ultrasonic B-mode image signal obtained from the transmission/reception control circuit, a cursor setting device for supplying to the transmission/reception control circuit a cursor position signal in order to display a cursor at a predetermined scan position of the B-mode display, at least one echo tracking circuit for causing at least one marker to track the video signal of the moving member at a desired position on the cursor, at least one marker setting device for supplying to the echo tracking device an initial marker signal for setting the initial position of the marker on the cursor, a synthesizer for synthesizing and sending to the B-mode display the B-mode image signal from the transmission/reception control circuit and the marker image signal from the echo tracking circuit, a position measuring circuit for measuring the position of the moving member on the cursor on the basis of the marker image signal from the echo tracking circuit, a Doppler probe for transmitting/receiving a continuous ultrasonic wave to/from the portion under examination, a flow velocity detection circuit for detecting the flow velocity of a fluid in the moving member on the basis of the pick-up signal from the Doppler probe, an arithmetic processing circuit for commuting the flow velocity of the fluid in the moving member from the position signal from the position measuring circuit and the flow velocity signal from the flow velocity detection circuit, and a display for displaying the result of the computation by the arithmetic processing circuit.

Further, to realize the third object of this invention, there is provided an ultrasonic diagnostic apparatus wherein the ultrasonic pulse probe for producing the B-mode tomographic image and the Doppler probe are integrated as a single unit, transmitting/receiving vibrators provided in the ultrasonic pulse probe and a transmitting vibrator and at least one receiving vibrator provided in the Doppler probe are fixed in a prescribed positional relation, the B-mode scanning plane and the Doppler beam are disposed so as to approach and intersect at a desired depth in the portion under examination, and the ultrasonic pulse probe and the Doppler probe are driven by ultrasonic excitation pulses and a continuous wave, respectively, the two excitations being at different frequencies, whereby the angle between the Doppler beam and the direction of fluid flow in the portion under examination can be set to a desired magnitude on the basis of the clarity of the B-mode image.

BRIEF DESCRIPTION OF THE DRAWINGS

FIG. 4 is diagram for explaining the operation of the echo tracking circuit shown in FIG. 3.

DESCRIPTION OF THE PREFERRED EMBODIMENTS

Preferred embodiments of the invention will now be described with respect to the drawings.

Figure 1:
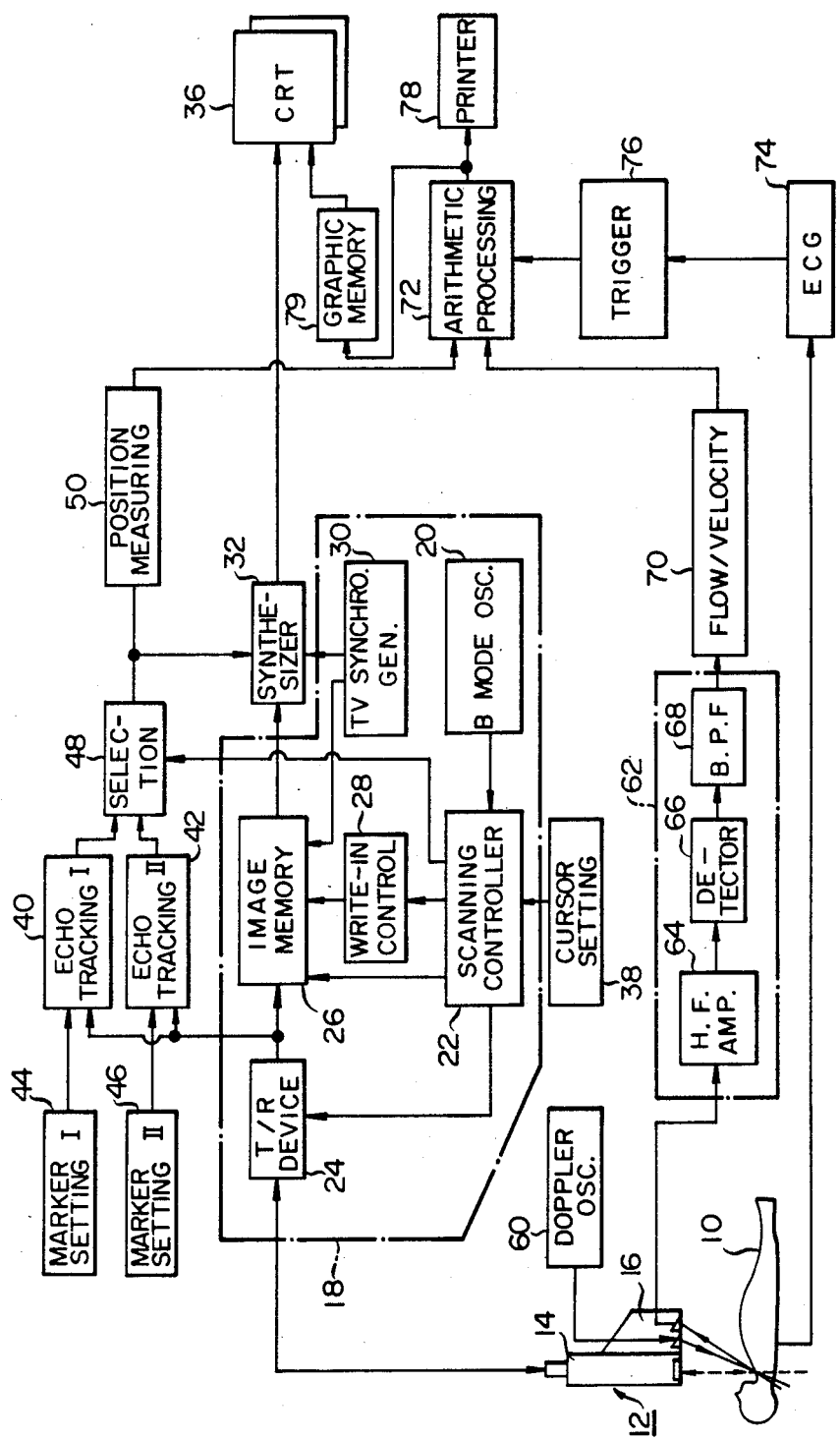
FIG. 1 is a schematic diagram of one embodiment of the ultrasonic diagnostic apparatus of this invention.

FIG. 1 shows the overall arrangement of the ultrasonic diagnostic apparatus of the invention. The apparatus provides a B-mode image display of a portion under examination of a subject 10 which includes a moving member, namely in this embodiment a carotid artery of the brain circulatory system, and at the same time provides data on the blood vessel diameter, blood flow velocity and blood flow volume relative to the carotid artery.

For the purpose of obtaining the B-mode display and measuring the blood vessel diameter, blood flow velocity and blood flow volume, a probe 12 is attached to the body of the subject 10 at a point in the vicinity of one of the carotid arteries. The probe 12 of this embodiment is an integrated probe including in a single unit an ultrasonic pulse probe 14 for producing the B-mode display and a Doppler probe 16 for detecting the blood flow velocity. The ultrasonic pulse probe 14 directs ultrasonic pulses toward the carotid artery and receives the echos reflected from the tissue boundaries of the artery, making it possible to obtain a luminance display of the tissues in the direction of depth on a CRT or other display device and, by scanning the transmitted/received pulse wave along a desired cross section, to obtain a desired B-mode tomographic image. In the embodiment, the ultrasonic pulse probe 14 is constituted as an electronic linear scanning probe. On the other hand, the Doppler probe 16 comprises a transmitting vibrator for directing a continuous ultrasonic wave into the carotid artery and a receiving vibrator for receiving the reflected wave which has been frequency shifted by the Doppler effect in accordance with the blood flow velocity in the carotid artery. The flow velocity of the blood in the carotid artery can be derived from this frequency shift.

B-mode image display

An explanation will first be given of the B-mode image display employing the ultrasonic pulse probe 14.

The transmission and reception of the ultrasonic pulse beam from the ultrasonic pulse probe 14 is controlled by a transmission/reception control circuit 18 which conducts electronic linear scanning control and also controls the focusing operation of the ultrasonic pulse beam as required.

The transmission/reception control circuit 18 includes a B-mode oscillatory 20 for producing an excitation signal of a frequency appropriate for the vibrator of the probe 14. This fundamental frequency from the B-mode oscillator 20 is subjected to predetermined frequency division in a scanning controller 22 thereby to obtain a repeat frequency (rate frequency) appropriate for the ultrasonic pulse beam. Electronic scanning control is carried out by means of this repeat frequency. Actual transmission/reception control of the probe 14 is carried out by a transmission/reception device 24 which operates in response to the repeat frequency from the scanning controller 22. The transmission/reception device also carries out focusing control of the pulse beam each time it is transmitted or received.

The pick-up signals obtained from the probe 14 are subjected to focusing control, together with a specific amount of delay, by the transmission/reception device 24 and, after being amplified and detected, are sequentially stored at specific addresses in an image memory 26 which may, for example, be a frame memory. This storage operation is controlled by a write-in control circuit 28 and a control signal from the scanning controller 22.

With this arrangement, once a given number of scans have been completed so as to store the image of a single scanning frame in the image memory 26, the stored data is read out at high speed by a read-out signal from a standard TV synchronizing signal generator 30. The read-out signal is used as a B-mode image signal.

In this embodiment, this B-mode image signal is synthesized with the synchronizing signal from the standard TV synchronizing signal generator 30 in a synthesizer 32 to produce a synthesized image signal which is forwarded to a B-mode display 36 constituted of a CRT etc. where it is displayed as a tomographic image along a specific scanning cross section.

Thus, in accordance with this embodiment, the B-mode pick-up signal from the probe 14 is first once stored in the digital image memory 26, and the read-out of the stored data on the read-out side is controlled by a TV synchronizing signal which is independent of the write-in side. Thus, the sweep speed in the display can be made many times faster than the ultrasonic scanning speed for write-in to the image memory 26 so that it is possible to obtain an ultrasonic tomographic image on the display 36 which is of high quality and free of flicker.

Figure 2:
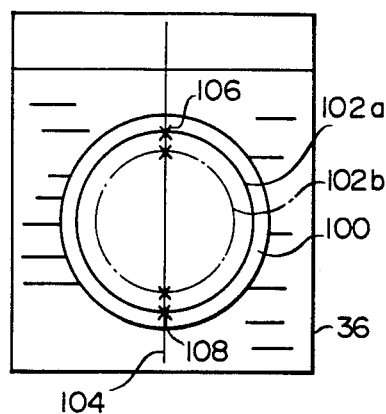
FIG. 2 is an explanatory view showing an example of a B-mode tomographic image obtained with the ultrasonic diagnostic apparatus of FIG. 1.

FIG. 2 shows one example of an image displayed on the B-mode display 36. The image shown is that obtained when the ultrasonic pulse beam is transmitted/received perpendicularly to the carotid artery. It will be noted that the carotid artery 100 is displayed as a tomographic image in which both the inner and outer walls of the artery appear with high clarity.

Measurement of blood vessel diameter

As is clear from the foregoing description, the apparatus according to this invention makes it possible to obtain a high-clarity B-mode tomographic image of the portion under examination (a carotid artery) on the display 36. However, if at the same time as observing this tomographic image it is also desired to observe the corresponding amount of blood flow, it will be indispensable to measure the inside diameter of the artery 100. In conventional apparatuses, this inner diameter is determined by measurement from an A-mode picture. In the present invention, however, it can be measured automatically. What requires attention in the measurement of the artery diameter is that the diameter of the artery 100 changes with the constant, alternate expansion and contraction thereof with the pulsation of the circulatory system, making it necessary to carry out the measurement while following the variation in diameter without delay.

In FIG. 2 the reference numerals 102a and 102b denote the positions of the inner wall of the artery 100 at the time of expansion and contraction, respectively. In this invention, this movement is tracked using the echo tracking method.

More specifically, as shown in FIG. 2, a cursor 104 is displayed within the image appearing on the display 36 so as to pass through approximately the center of the artery 100 and two markers 106 and 108 are made to appear at the two points of intersection of the cursor 104 with the inner wall 102 of the artery 100. Thus, if it should be possible to have these markers track the movement of the inner wall 102, it would be possible to automatically determine the diameter of the artery from the distance between the markers 106 and 108.

In this embodiment, the cursor 104 is established by having the scanning controller 22 supply to the image memory 26, separately from the pick-up signal from the probe 14, a luminance signal with respect to a specific scanning position. In this case, the position of the cursor 104 is selectively determined by a cursor setting device 38. In this embodiment, the cursor 104 is fixed at the center of the displayed picture and in actual operation the position of attachment of the probe 12 on the subject under examination is selected so as to cause the image of the artery 100 to be centered on the cursor 104. If desired, it is of course also possible to arrange for the cursor 104 to shift to the desired position with respect to the B-mode image of the artery 100 after this image has been displayed.

The present invention further provides an echo tracking circuit in order to make it possible to display the markers 106, 108 at positions corresponding to the inner wall 102 of the artery 100 and to cause these markers to follow the movement of the inner wall. In this particular embodiment, there are provided two echo tracking circuits 40, 42, one for each of the markers. Both of the echo tracking circuits 40, 42 are supplied with a luminance signal, namely that along the cursor 104. Further, for setting the initial position of the markers, the echo tracking circuits 40, 42 are supplied with initial marker setting signals from marker setting devices 44, 46, respectively. The outputs from the echo tracking circuits 40, 42 are sent to a selection circuit 48 and then are independently forwarded to the synthesizer 32 when the selection circuit 48 receives a selection signal from the scanning controller 22. The selected signal is then sent to a position measuring circuit 50 (to be described later) where the position of the moving member (in this embodiment, the inner diameter of the artery 100) is measured.

More specifically, in this embodiment, the output of the position measuring circuit 50 is supplied to a printer 78 which prints out the calculated result and is also supplied to the synthesizer 32 which, when required, simultaneously displays it with the B-mode picture.

Figure 3:
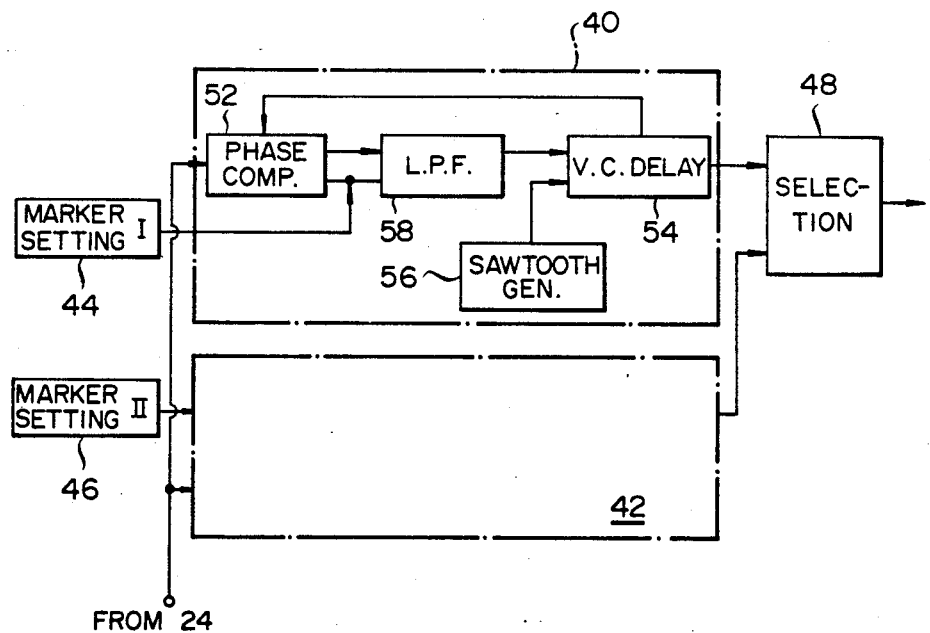
FIG. 3 is a block diagram showing a specific circuit arrangement for the echo tracking circuit in the ultrasonic diagnostic apparatus of FIG. 1.

The details of the echo tracking circuits 40, 42 are shown in FIG. 3. As the two circuits are identical, only the arrangement of the echo tracking circuit 40 for the marker 106 will be explained in the following.

The echo tracking circuit 40 is basically a phase lock loop circuit. The picture signal initially set by the marker 106 on the cursor 104 is compared with the output of a voltage controlled delay circuit (VCD) 54 in a phase comparator 52 and the phase of the VCD 54 is adjusted to keep the two signals coincident at all times. The output phase of the VCD 54 is controlled by the initial marker setting signal from the marker setting device 44 and the value of the output of a sawtooth wave generator 56, and the VCD 54 produces a delayed output consisting of a tracking gate pulse having a pulse width which is one half the wavelength of the ultrasonic excitation signal from the B-mode oscillator 20. In this embodiment the delay of this output corresponds to the depth of the inner wall 102 of the artery 100 from the outer surface of the subject under examination and by having the VCD 54 vary this delay time so as to track the movement of the inner wall, it is possible by outputting this delay time to hold the marker 106 constantly on the inner wall 102 of the artery 100. It is noted that the output of the phase comparator 52 is fed to the VCD 54 through a low pass filter 58.

FIG. 4 shows the operation of the echo tracking circuit 40. The fundamental frequency of the ultrasonic pulse beam transmitted/received by the ultrasonic pulse probe 14 is fixed by the B-mode oscillator 20. As shown by the magnified view of a single wave of this excitation signal shown in FIG. 4a, the phase of the wave shifts from that shown by the solid line in the figure toward that shown by the chain line as the position of the artery 100 shifts.

As mentioned above, the gate pulse produced by the VCD 54 (FIG. 4b) of the echo tracking circuit 40 has a pulse width which is one half the wavelength of the excitation signal wave. The marker 106 is in advance positioned in the picture by the initial marker setting signal from the marker setting device 44 so as to fall at one of the two points of intersection between the cursor 104 and the inner wall 102 of the artery 100 at the beginning of tracking. As a result, the delay time represents the distance between the surface of the subject and the marker position, whereby it will be understood that the gate pulse of FIG. 4b is located at a picture signal position corresponding to the inner wall on one end of the cursor 104.

The phase comparator 52 compares the wave form shown in FIG. 4a with the gate pulse shown in FIG. 4b and when this is integrated in the low pass filter 58, then, in the case where the gate pulse b accurately tracks the solid line of the wave form a, the integrated portion indicated by hatching in FIG. 4c will be constituted of equal positive and negative parts so that the output of the low pass filter will be zero. As a result, the output of the comparator by the comparison with the sawtooth wave will remain unchanged and the delay time will also stay the same.

On the other hand, when the received wave shifts in the direction of the chain line in FIG. 4a, the output of the low pass filter 58 becomes positive as shown in FIG. 4d, the delay time of the VCD 54 is reduced by the same extent and the gate pulse tracks so as to make the integrated value of the received wave shown by the chain line become zero. Therefore, the marker 106 appearing within the picture as shown in FIG. 2 constantly tracks the inner wall, while the integrated value at this time is output as a signal indicating the distance of the inner wall from the surface of the subject.

In the present embodiment, two markers 106, 108 are provided at diametrically opposite points on the inner wall and the display signals for these markers and the depth data are sequentially switched over and selected in the selection circuit 48 by the selection signal from the scanning controller 22. Consequently, in addition to reading the B-mode image signal including the signal for the cursor 104 from the image memory 26, the synthesizer 32 also reads the data for the markers 106, 108 appearing on the cursor 104 from the selection circuit 48 and synthesizes these signals for display on the display 36. Thus it is possible to display a cross sectional view of the carotid artery including markers that constantly track the inner wall of the artery as shown in FIG. 2. Moreover, as mentioned above, the difference between the positions of the two points of the inner wall indicated by the markers is calculated by the position measuring circuit 50, whereby it is possible to output the constantly changing diameter of the artery as it changes from instant to instant.

Detection of blood flow velocity

A continuous untrasonic excitation wave is supplied to the transmitting vibrator of the Doppler probe 16 from a Doppler oscillator 60 and the continuous ultrasonic wave is transmitted from the surface of the probe to pass through the carotid artery or other blood vessel. As a result, in the present invention, it is not only possible to obtain partial velocity information as in ordinary pulse Doppler systems but also possible to detect the average flow value over the whole area for each instant. Moreover, as the frequency of the continuous wave produced by the Doppler oscillator 60 differs from that of the ultrasonic pulses for B-mode image display, there is also the advantage that it is possible to measure both simultaneously.

The continuous ultrasonic wave is reflected by the blood, particularly by the erythrocytes, flowing in the blood vessel and is subject to the Doppler effect in proportion to the flow velocity. The reflected wave which has been frequency shifted by the Doppler effect is received by the receiving vibrator provided in the Doppler probe 16 and the resulting signal is electrically processed by a Doppler processing circuit 62. The Doppler processing circuit 62, which includes a high frequency amplifier 64, a detector 66 and a band pass filter 68, extracts only the blood flow velocity signal and sends this to a flow velocity detection circuit consisting of a frequency/voltage conversion circuit, where the Doppler beat, which is proportional to the blood flow velocity, is converted to a voltage signal.

In this way, the blood flow velocity is detected in real time by means of the Doppler effect.

Measurement of flow amount

As is clear from the foregoing explanation, the diameter of the blood vessel can be obtained from the position measuring circuit 50 and the blood flow velocity can be obtained from the flow velocity detection circuit 70. These two values are input to an arithmetic processing circuit 72 which carries out a prescribed calculation whereby it is possible to electrically obtain the amount of blood flow at each instant. As the arithmetic processing circuit 72 it is possible to employ a microprocessor and, moreover, it is also possible to have the processing operations of the position measuring circuit 50 and the flow velocity detection circuit 70 carried out by the arithmetic processing circuit 72. The arithmetic processing circuit 72 is capable of sequentially processing input data in accordance with a prescribed processing cycle and in the present embodiment this processing timing is controlled in synchronism with a biological signal from the subject 10, and for this there is used the ECG (electrocardiogram) signal from the subject 10. More specifically, an ECG circuit 74 detects the pulse of the subject 10 and produces an ECG signal which controls a processing trigger circuit 76 in such a way that it supplies trigger signals to the arithmetic processing circuit 72 in synchronism with the pulse of the subject 10. The computation of the blood flow amount is carried out with this timing.

The signal representing the amount of blood flow is sent to the printer 78 for print-out and is also simultaneously displayed on the B-mode display 36 via a graphic display memory 79. It can also be displayed on a graphic display separate from the B-mode display 36.

Further, it is also possible to provide the B-mode display 36 with two screens and display the blood flow amount data and other information on a separate screen from the screen for ordinary image display.

Structure of the probe

With the arrangement described above it is possible to observe and examine a desired moving member as a B-mode tomographic image while also observing the amount of fluid flowing through the same member by dint of a real-time computation of said flow amount. One aspect of this invention that enhances this capability is the probe 12, which is designed to facilitate the proper transmission into and reception from the portion under examination of the ultrasonic waves for B-mode image display and for Doppler detection. A preferred embodiment of this probe will now be described below.

Figure 5:
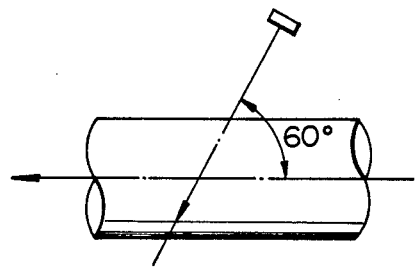
FIG. 5 is an explanatory view showing the relation between the direction of blood flow and the direction of the Doppler beam.

It is well known that when the flow velocity of blood or other fluid is to be measured by a method employing the Doppler effect, the angle of the ultrasonic wave to the direction of flow is a critical factor and that, as shown in FIG. 5, the best results are obtained when this angle is 60°.

In general, however, it is not possible to judge the direction in which a blood vessel lies in a living body. With the conventional apparatuses it has been only possible to presume the direction of the blood vessel to be subjected to measurement and then to attach the Doppler probe to the subject so as to form an angle of approximately 60° relative to this presumed direction. As a result, the conventional apparatuses have had the drawback of entailing a large error component in the measurement of the blood flow velocity using the Doppler effect.

Figure 6:
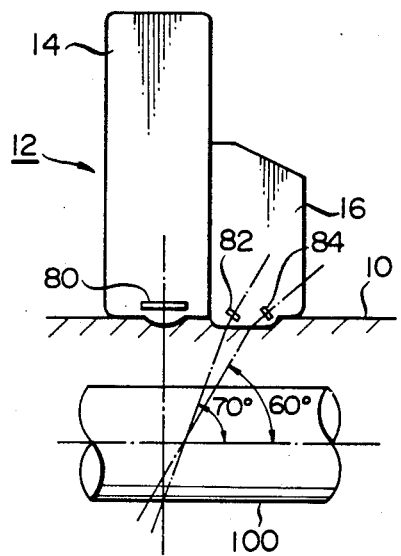
FIG. 6 is schematic view of one embodiment of an integrated probe used in the present invention.
Figure 7:
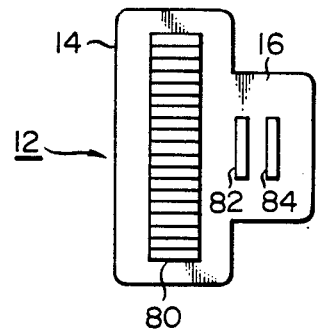
FIG. 7 is a plan view of the surface of a vibrator of the integrated probe of FIG. 6.

The probe 12 used in the present invention is illustrated in FIGS. 6 and 7. The probe 12 comprises both the ultrasonic pulse probe 16 for producing the B-mode tomographic image and the Doppler probe 16 for measurement of the blood flow velocity as integrated into a single unit. This probe 12 is attached at the desired position on the body of the subject 10 and is used to transmit/receive an ultrasonic pulse beam and an ultrasonic continuous wave to/from a blood vessel 100, typically a carotid artery.

In this embodiment the ultrasonic pulse probe 14 is constituted as an electronic linear scanning probe and, as shown in FIG. 7, comprises a plurality of ceramic vibrators 80 arranged in a single row. By electronically scanning these ceramic vibrators it is possible to carry out tomographic scanning in a manner cutting across the artery 100. The scanning width of the row of vibrators 80 is therefore made greater than the diameter of the artery 100.

In this embodiment, the vibrators 80 of the ultrasonic pulse probe 14 are supplied with ultrasonic excitation pulses of a frequency of 5 MHz.

On the other hand, the Doppler probe 16 comprises a transmitting vibrator 82 and a receiving vibrator 84 located in close juxtaposition. In this embodiment, the transmitting vibrator 82 is driven by a continuous ultrasonic excitation wave of a frequency of 7.5 MHz and the continuous ultrasonic wave directed into the subject 10 is reflected by the blood (particularly the erythrocytes) flowing in the artery. The reflected ultrasonic wave, which is frequency shifted by the Doppler effect to an extent which is proportional to the blood flow velocity, is then electrically picked up by the receiving vibrator 84, In this embodiment, the transmitting vibrator 82 and the receiving vibrator 84 are fixed so as to form angles with the direction of blood flow of 70° and 60° at the time the direction of transmission/reception of the ultrasonic pulse beam is set perpendicular to the direction of blood flow.

As in this embodiment the ultrasonic pulse probe 14 for B-mode display and the Doppler probe 16 for measurement of blood flow velocity are integrally formed as a single unit in the probe 12, the probes 14 and 16 are held in a fixed positional arrangement, making it possible for them to cooperate most effectively in carrying out B-mode imaging and Doppler detection.

This will now be explained in more detail. As was mentioned earlier with respect to FIG. 2, the B-mode image obtained from the ultrasonic pulse probe 14 is displayed on a screen as a cross section of the artery 100. And at this time the portion of the subject 10 through which the Doppler beam from the Doppler probe passes is substantially the same portion of the artery as that displayed on the screen as shown in FIG. 2. Therefore, if the cross section displayed as a B-mode image is perpendicular to the direction of blood flow, the Doppler beam will automatically be transmitted and received at the proper angle with respect to the direction of blood flow. As a result, the measured blood flow velocity obtained by the Doppler effect will accurately represent the actual blood flow velocity in the artery 100.

One feature characterizing the present invention is that the cross section of the artery 100 is displayed as a B-mode image. As is well known, in the case of B-mode imaging, the image of highest clarity is obtained when the ultrasonic pulse beam is transmitted/received perpendicularly to the plane of the tissue boundary in the subject. This of course applied as well to the wall of the artery 100.

Therefore, in positioning the probe 12 on the subject 10, the operator of the apparatus according to this invention need only observe the B-mode image displayed as shown in FIG. 2 while adjusting the position of the probe to obtain the tomographic image of the artery 100 of highest clarity. This will assure that the pulse beam is accurately directed perpendicularly to the artery 100 and that, as a natural result, the vibrators 82, 84 of the Doppler probe which are fixed in a predetermined positional relation with respect to the ultrasonic pulse probe 14 are oriented properly with respect to the direction of blood flow in the artery 100. The blood flow velocity reading obtained at this time can be used without compensation as the final measured value.

Consequently, the present invention has merits in that the blood flow velocity can be measured with little error and that the attachment of the probe 12 can be carried out very easily From the foregoing it will be understood that in accordance with the present invention the proper positioning of the probe can be accurately determined with reference to the clarity of the B-mode image, which in turn makes it possible to greatly enhance the precision with which the blood flow velocity can be measured by use of the Doppler effect. Moreover, as any possible interference between the ultrasonic pulse probe and the Doppler probe is precluded by providing them with separate driving frequency sources, it is possible to carry out transmission and reception with both probes simultaneously, thus making it possible to obtain both the B-mode image and the blood flow velocity in real time.

Figure 8:
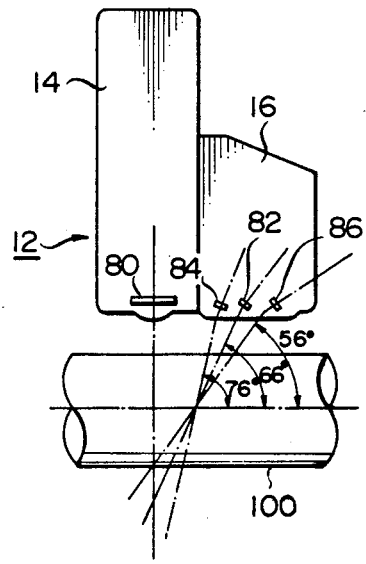
FIG. 8 is a schematic view of another embodiment of an integrated probe.
Figure 9:
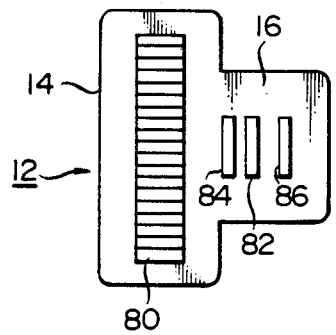
FIG. 9 is a plan view of the surface of a vibrator of the integrated probe of FIG. 8.

FIGS. 8 and 9 show another embodiment of a probe integrally combining an ultrasonic pulse probe and a Doppler probe in a single unit. Here like members to those shown in FIGS. 6 and 7 are denoted by like reference numerals and no further explanation of these members will be given.

The probe of this embodiment is characterized in that the Doppler probe 16 is provided with two receiving vibrators. Namely, receiving vibrators 84 and 86 are provided on opposite sides of the transmitting vibrator 82 each at a prescribed distance therefrom. The wave reflected from the artery 100 is received simultaneously by both of the receiving vibrators 84, 86. The angles formed by the vibrators 82, 84 and 86 with respect to the direction of blood flow are selected as 66°, 76° and 56°.

By provision of the two receiving vibrators 84, 86 it is possible to reduce the adverse effect that would arise should the angle between the direction of ultrasonic Doppler beam transmission/reception and the direction of blood flow vary from the well-known optimum angle of 60°. Moreover, similarly to the case of the preceding embodiment, the fact that the Doppler probe 16 and the ultrasonic pulse probe 14 are combined in a single unit makes it possible to realize highly accurate measurement of the blood flow velocity by selecting the position of attachment of the probe 12 so as to obtain a B-mode image of optimum clarity.

EFFECT OF THE INVENTION

With the ultrasonic diagnostic apparatus as described in the foregoing, a cursor can be displayed at a prescribed scanning position of a B-mode picture, markers can be provided at the points of intersection between the cursor and a prescribed moving member under examination, these markers can be made to track the movement of the moving member, as a result the position of the moving member can be displayed on a B-mode picture and can also be output electrically, and as a further result the position of the moving member can be electrically stored or arithmetically processed, so that the apparatus has particularly high utility in the measurement of blood vessel diameter or blood flow amount in the circulatory system and, in the measurement of the volume of internal organs etc.

Moreover, in accordance with the apparatus of the present invention, it is possible to combine the results of the B-mode image display with the results of the measurement of the blood flow velocity using the Doppler effect of a continuous ultrasonic wave to obtain an accurate real-time reading of the amount of blood flow in a given portion of a subject under examination. As the apparatus is thus able to measure the amount of blood or other fluid flowing in the subject with high precision, it is especially useful for obtaining optimum diagnostic information with respect to the circulatory system.

Further, in accordance with this invention, an ultrasonic pulse probe for B-mode imaging and a Doppler probe are integrated in a single body so that the B-mode scanning plane and the Doppler beam will approach and intersect at a desired depth in the portion under examination. Because of this arrangement, it is possible to set the angle between the direction of Doppler beam transmission/reception and the direction of fluid movement within a moving member at a desired magnitude, making the apparatus of this invention highly useful for the measurement of flow velocity and the like.

Although in the embodiments described above, the measurements were described as being carried out with respect to blood, the present invention is not limited to measurement and imaging related to blood and blood vessels and can also be applied effectively to the imaging of other organs and the measurement of the flow velocities and flow amounts of other body fluids than blood.

What is claimed is:

1. An ultrasonic diagnostic apparatus comprising an ultrasonic probe which transmits and receives an ultrasonic wave signal to and from a portion under examination which includes a moving member, a transmission and reception circuit coupled to said ultrasonic probe for controlling the pulse transmission and reception operation of the ultrasonic probe, a B-mode display for displaying a B-mode tomographic image in accordance with an ultrasonic B-mode image signal received from the transmission and reception control circuit, a cursor setting device for supplying to the transmission and reception control circuit a cursor position signal in order to display a cursor at a desired scan position of the B-mode display, at least one echo tracking circuit coupled to said B-mode display for causing at least one marker to track the video signal of the moving member at a desired position on the cursor in response to the receipt of an initial marker signal, at least one marker setting device for supplying to the echo tracking device said initial marker signal for setting the initial position of the marker on the cursor, a synthesizer coupled to said transmission and reception control circuit and said echo tracking circuit for synthesizing and sending to the B-mode display the B-mode image signal from the transmission and reception control circuit and the marker image signal from the echo tracking circuit, and a position measuring circuit coupled to said echo tracking circuit for measuring the position of the moving member on the cursor in accordance with the marker image signal from the echo tracking circuit.

2. An ultrasonic diagnostic apparatus as claimed in claim 1 wherein the ultrasonic pulse probe is an electronic linear scanning probe.

3. An ultrasonic diagnostic apparatus as claimed in claim 1 wherein the transmission and reception control circuit comprises a B-mode oscillator which produces an ultrasonic excitation frequency for the vibrators of the ultrasonic probe and this excitation frequency is frequency divided to obtain a prescribed frequency and in response thereto the ultrasonic probe is electronically scan controlled.

4. An ultrasonic diagnostic apparatus as claimed in claim 1 wherein the transmission and reception control circuit comprises an image memory into which the received signals from the transmission and reception control circuit are sequentially written until one frame of the image has been stored therein, whereafter the stored data is read out at high speed as a B-mode image signal.

5. An ultrasonic diagnostic apparatus as claimed in claim 1 wherein the echo tracking circuit comprises a phase comparator and a voltage controlled delay circuit, the phase comparator for comparing the image signal initially set by the marker on the cursor with the output of the voltage controlled delay circuit and for controlling the output phase of the voltage controlled delay circuit so as to maintain the two signals in coincidence with each other at all times.

6. An ultrasonic diagnostic apparatus comprising an ultrasonic probe which transmits and receives an ultrasonic wave signal to and from a portion under examination which includes a moving member, a transmission and reception circuit coupled to said ultrasonic probe for controlling the pulse transmission and reception operation of the ultrasonic probe, a B-mode display for displaying a B-mode tomographic image in accordance with an ultrasonic B-mode image signal received from the transmission and reception control circuit, a cursor setting device for supplying to the transmission and reception control circuit a cursor position signal in order to display a cursor at a predetermined scan position of the B-mode display, at least one echo tracking circuit coupled to said B-mode display for causing at least one marker to track the video signal of the moving member at a desired position on the cursor in response to the receipt of an initial marker signal, at least one marker setting device for supplying to the echo tracking device said initial marker signal for setting the initial position of the marker on the cursor, a synthesizer coupled to the transmission and reception control circuit and said echo tracking circuit for synthesizing and sending to the B-mode display the B-mode image signal from the transmission and reception control circuit and the marker image signal from the echo tracking circuit, a position measuring circuit coupled to said echo tracking circuit for measuring the position of the moving member on the cursor in accordance with the marker image signal from the echo tracking circuit, a Doppler probe for transmitting and receiving a continuous ultrasonic wave to and from the portion under examination, a flow velocity detection circuit coupled to said Doppler probe for detecting the flow velocity of a fluid in the moving member in accordance with the received signal from the Doppler probe, an arithmetic processing circuit for computing the flow amount of the fluid in the moving member from the position signal from the position measuring circuit and the flow velocity signal from the flow velocity detection circuit, and a display coupled to said arithmetic processing circuit for displaying the result of the computation by the arithmetic processing circuit, whereby the flow velocity and flow amount of the fluid in the moving member can be displayed in real time simultaneously with a B-mode image of the portion under examination including the moving member.

7. An ultrasonic diagnostic apparatus as claimed in claim 6 wherein the ultrasonic pulse probe is an electronic linear scanning probe.

8. An ultrasonic diagnostic apparatus as claimed in claim 6 wherein the transmission and reception control circuit comprises a B-mode oscillator which produces an ultrasonic excitation frequency for the vibrators of the ultrasonic probe and this excitation frequency is frequency divided to obtain a prescribed repeat frequency and in response thereto the ultrasonic probe is electronically scan controlled.

9. An ultrasonic diagnostic apparatus as claimed in claim 6 wherein the transmission and reception control circuit comprises an image memory into which the received signals from the transmission and reception control circuit are sequentially written until one frame of the image has been stored therein, whereafter the stored data is read out at high speed as a B-mode image signal.

10. An ultrasonic diagnostic apparatus as claimed in claim 6 wherein the echo tracking circuit comprises a phase comparator and a voltage controlled delay circuit, the phase comparator for comparing the image signal initially set by the marker on the cursor with the output of the voltage controlled delay circuit and for controlling the output phase of the voltage controlled delay circuit so as to maintain the signals in coincidence with each other.

11. An ultrasonic diagnostic apparatus as claimed in claim 6 wherein the computation timing of the arithmetic processing circuit is controlled in synchronism with a biological signal from the subject.

* * * * *